United States Patent [19]

Minisci et al.

[11] 4,423,263

[45] Dec. 27, 1983

[54] PROCESS FOR THE SIDE-CHAIN POLYHALOGENATION OF POLYALKYLAROMATIC HYDROCARBONS

[75] Inventors: Francesco Minisci, Milan; Giancarlo Serboli, Saronno; Edoardo Platone, San Donato Milanese, all of Italy

[73] Assignee: ANIC, S.p.A., Palermo, Italy

[21] Appl. No.: 393,441

[22] Filed: Jun. 29, 1982

Related U.S. Application Data

[63] Continuation of Ser. No. 279,260, Jul. 1, 1981, abandoned.

[30] Foreign Application Priority Data

Jul. 15, 1980 [IT] Italy .............................. 23440 A/80

[51] Int. Cl.$^3$ ...................... C07C 21/24; C07C 17/14
[52] U.S. Cl. .................................. 570/197; 570/196
[58] Field of Search ............................. 570/196, 197

[56] References Cited

U.S. PATENT DOCUMENTS

| | | | |
|---|---|---|---|
| 4,226,783 | 10/1980 | Marsh | 570/197 |
| 4,331,821 | 5/1982 | Schubart et al. | 570/197 |
| 4,348,265 | 9/1982 | Strom | 570/197 |

FOREIGN PATENT DOCUMENTS

| | | | |
|---|---|---|---|
| 45423 | 8/1980 | European Pat. Off. | 570/197 |
| 45425 | 8/1980 | European Pat. Off. | 570/197 |
| 55-79332 | 6/1980 | Japan | 570/197 |
| 2080299 | 2/1982 | United Kingdom | 570/197 |

OTHER PUBLICATIONS

Minisci et al., (R): Tetrahedron Letters, 699, (1966).
Minisci et al., Tetrahedron Letter, 4663, 4667, (1965).
Burton et al., Comprehensive Organic Chemistry, (1979), pp. 275–278, vol. 2.

*Primary Examiner*—Delbert E. Gantz
*Assistant Examiner*—A. Pal
*Attorney, Agent, or Firm*—Morgan, Finnegan, Pine, Foley & Lee

[57] ABSTRACT

A process for the selective side-chain halogenation of alkylaromatic hydrocarbons, consisting of reacting the hydrocarbon with an N-halogenoamine in the presence of a proton donor and a metal ion.

7 Claims, No Drawings

PROCESS FOR THE SIDE-CHAIN POLYHALOGENATION OF POLYALKYLAROMATIC HYDROCARBONS

The present application is a continuation of application Ser. No. 279,260, filed July 1, 1981, now abandoned.

This invention relates to a process for the selective side-chain halogenation of alkylaromatic hydrocarbons, consisting of reacting the respective hydrocarbon with an N-halogenoamine in the presence of a proton donor and a catalyst constituted by an ion which derives from a metal possessing various oxidation states, but which is in a lower oxidation state. In particular, this invention relates to a process which enables a single halogen atom for each side chain to be introduced successively or simultaneously into the alpha carbon of all the alkyl chains bonded to polyalkylated aromatic nuclei. It is well known that the introduction of halogens into the side chains of alkylaromatic hydrocarbons requires the presence of radical reactants or initiators ("Free Radicals" J. K. Kochi editor, New York 1973; D. C. Nonhebel, J. C. Walton, "Free Radical Chemistry" Cambridge 1974), for example the use of luminous radiation or peroxides, N-bromoamides, or tert-alkyl-hypohalogenites. These agents ensure easy entry of the first halogen atom into one of the alkyl chains. Subsequently, when the reaction conditions are forced in order to introduce other halogen atoms into the other alkyl groups bonded to the aromatic nucleus partly deactivated by the first substitution, a polyhalogenated derivative is obtained (one halogen for each alkyl group) with generally unsatisfactory selectivity, in that the tendency for the halogenation of the subsequent alkyl groups competes with the tendency for the introduction of other halogen atoms into the already halogenated alkyl.

Other competitive reactions which further lower selectivity are the nuclear halogenation and Friedel-Craft condensation between halogenoalkylaromatics and unsubstituted aromatic nuclei. Recently, a new functionalising method, which uses halogenoamines in proton donor means with metal redox systems able to generate radical cations, has allowed halogenation of paraffin systems with good selectivity, and the nuclear amination and side-chain halogenation of alkylaromatics (e.g. Synthesis 1973, 1; Tetrahedron Letters 7, 1966, 699; Journal of the Chemical Society, Perkin II, 1974, 416; Tetrahedron Letters 43, 1964, 3197; Tetrahedron Letters 51, 1966, 4663 etc.). It has now been surprisingly found, and constitutes the subject matter of the present invention, that it is possible to effect the halogenation with N-halogenoamines and to obtain, with very high selectivity, polyhalogenated derivatives of alkylaromatic hydrocarbons containing one halogen atom in each alkyl side chain, this halogen atom being bonded to the alkyl chain carbon atom connected to the aromatic nucleus. Furthermore, with the same method, it is possible to effect the selective chlorination of the alpha position of the side chain of monoalkylaromatic hydrocarbons. The concurrent nuclear chlorination and amination reactions are thus minimised, and in addition by operating under mild conditions any polyhalogenation of the said alkyl group is prevented. The polyhalogenated derivatives containing one halogen for each alkyl are obtained with practically quantitative conversions of the alkylaromatic hydrocarbon, and with very high yields, even for those hydrocarbons which are particularly unfavourable in terms of the mutual position of the substituents. The monohalogeno and polyhalogeno derivatives obtainable by the process according to the present invention represent raw materials and intermediates of maximum importance, especially in the preparation of monomers and polymer modifiers. Thus for example, using $\alpha, \alpha'$-dichloroxylene it is possible with conventional methods (e.g. direct amination with ammonia) to obtain meta-xylylenediamine, which is largely used in the synthesis of polyamides and copolyamides, as a urethane polymer modifier etc. (Industrial and Engineering Chemistry, 49, 1957, 1239; Journal of Polymer Science A-2,4,1966,959; Condensation Monomers, J. K. Stille and T. W. Campbell eds New York 1972). As stated, the process according to the present invention is carried out by reacting a polyalkylaromatic hydrocarbon with a N-halogenoamine in the presence of a proton donor and a catalyst constituted by an ion which is derived from a metal able to exist in various oxidation states, but which is in a lower oxidation state.

The reaction can take place in a suitable solvent medium, or the actual proton donor can constitute the reaction medium. The N-halogenoamine must derive from a secondary amine with sufficient steric bulk and chains which do not contain carbon-hydrogen bonds in the nitrogen delta position. In particular, this amine can be chosen from diisopropylamine, diisobutylamine, diterbutylamine, dipropylamine, dicyclohexylamine, cyclohexylpropylamine, cyclohexylmethylamine, cyclohexylethylamine, tetramethylperidine, piperidine, dibenzylamine, benzylethylamine or benzylpropylamine. The synthesis of the halogenoamine can be conveniently carried out starting from a hypohalogenite of an alkaline or alkaline-earth metal (particularly sodium or calcium), carrying out the reaction in the presence of an organic solvent which can be the actual polyalkylaromatic hydrocarbon which is to be halogenated in the side chain.

The halogenation reaction must in its turn be carried out with careful temperature control, preferably between $-20°$ and $+40°$ C., the lower limit to the choice of temperature deriving both from the slowing down of the reaction and from a considerable increase in the viscosity of the medium which makes stirring difficult. Increasing the temperature beyond the aforesaid limit does not prevent the side-chain halogenation reaction, but can cause an increase in the nuclei halogenation and other secondary reactions. The applicant is convinced that the polyhalogenation reaction according to the present invention is of absolutely general application, and any polyalkylaromatic hydrocarbon can be modified as described in the present description. The following can be mentioned as examples of substrates; m-xylene, p-xylene, o-xylene, m-diisopropylbenzene, p-diisopropylbenzene, o-, m-, p-diethylbenzene. In the particular case of m-xylene (and of all the more unfavourable substrates), it is advisable to keep the temperature between $-10°$ and $+10°$ C. In all cases it is advisable to maintain effective stirring for the double purpose of keeping the reaction mass homogeneous and of rapidly dispersing the heat which can form locally by exothermic phenomena. As stated, the polyhalogenation reaction takes place in the presence of a proton donor. This can be chosen from a wide list of names, even though it is preferable to restrict the field to acetic acid, trifluoroacetic acid and the halogenoacetic acids in general, their mixtures and in particular sulphuric acid (including in mixture with the preceding). Its concentration at the beginning of the reaction is preferably chosen between 80 and 96%, this concentration being calculated taking account of all the diluting effects which can derive from adding the various ingredients.

The reaction between the polyalkylaromatic hydrocarbon and the N-halogenoamine can take place by photochemical initiation or, preferably, in the presence of a catalyst which, as stated, is constituted by a metal ion which derives from a metal having various possible oxidation states, but which is in a lower oxidation state. Among these, it is preferable to use an ion chosen from $Cu^+$, $Fe^{++}$, $Cr^{++}$, $Ti^{+++}$ or $V^{++}$. This catalyst can be present in a quantity variable from 1 to 50 mol % with respect to the alkyl side chains to be halogenated, and the proton donor is added in a molar ratio of between 1.2 and 8 with respect to the amine. The N-halogenoamine is used to the extent of 1 mole for each alkyl chain to be halogenated. The reaction can be carried out in the actual proton donor or it can sometimes be convenient to use other dilution agents. These can be chosen from esters, halogenated hydrocarbons, nitriles or nitro derivatives. For example, carbon tetrachloride, methyl formate, chlorobenzene, nitromethane, nitrobenzene or acetonitrile can be used. Without wishing to suggest any sequence of operations, which the expert of the art will be able to decide on the basis of his knowledge, it is considered advisable to introduce into the reaction environment firstly the metal salt and proton donor, followed slowly by the reagent mixture. The experimental conditions stated in the preceding description and in the examples given hereinafter should be evaluated globally on the basis of the high applicational value of the performance obtainable. A further positive characteristic of the method, which is very interesting from the industrial point of view because it provides a wide margin of flexibility to the production procedure, is the possibility of carrying out the polyhalogenation either in a single state or in a number of successive stages. For example, the α, α'-dichloroxylene can be obtained with good yield in a single step. Alternatively the reaction can be conducted to give medium yields of dichloroxylene and the like in monochloroxylene, then separating the crude monochloroxylene using distillation carried out under non-severe conditions, then returning it to the reaction either alone or mixed with fresh m-xylene.

Other details of the process according to the present invention will be apparent from analysing the operational examples. It will then be simple for the expert to extrapolate all the possibilities which the described technology offers in the alkylaromatic substitution field. From the procedures and considerations suggested in the present description it will be simple to derive the method for reacting other substrates of a similar nature, or for adapting the operational conditions to the particular requirements of individual cases.

The examples have an illustrative character, and the invention must in no way be considered limited thereby.

EXAMPLE 1

(a) 63.6 g (0.6 moles) of meta-xylene and 151.5 g (1.5 moles) of diisopropylamine are fed into a 3 l glass flask fitted with a thermometer, dropping funnel, mechanical air stirrer with glass blades and a bulb condenser. 2633 g of NaClO (containing 13% of active chlorine) are fed from the dropping funnel while maintaining the temperature at about 20° C. After the addition is complete, the organic phase is separated and washed with a solution of 8 g NaCl in 80 ml $H_2O$. A portion is withdrawn and subjected to iodometric titration to verify that the amine has been completely converted into chloroamine.

(b) 67.2 g (0.24 moles) of $FeSO_4.7H_2O$ and 480 g (4.9 moles) of 98% $H_2SO_4$ are fed into a 2 l flask fitted with a mechanical air stirrer with a half-moon teflon blade, thermometer, nitrogen inlet, jacketed dropping funnel and a reflux condenser. It is degassed with nitrogen and cooled to $-10°$ C. by means of an external refrigerant bath. The feed of the solution of chloroamine in xylene is then commenced from the funnel, which is cooled to about 0° C., and the addition is regulated in such a manner that the temperature in the flask remains around 0° C. The addition is complete in about 20 mins. Stirring is continued (maintaining 0° C.) for a further 40 mins. The reaction mixture is then poured into a beaker containing ice, under stirring.

When the addition is complete, the ice is allowed to dissolve, and the mixture is then repeatedly extracted with ether. The ether phases are combined and dried over $Na_2SO_4$. The solid is filtered off, and the ether is evaporated in a Vigreux column at 600 mm pressure. The residue is distilled at 100 mm pressure in a Vigreux column. Four distilled fractions are collected and are analysed by the gas chromatograph. The residue remaining in the boiler is also analysed by the gas chromatograph using the internal standard method in order to take account of any heavies which do not elute under the analysis conditions. By this means, a total of 5.91 g (0.055 m) of m-xylene, 0.765 g (0.0054 m) of derivative monochlorinated in the nucleus, 57.91 g (0.412 m) of monochloroxylene (m-chloromethyltoluene), 17.87 g (0.102 m) of α, α'-dichloroxylene, and 1.33 g (0.0084 m) of mixed polychlorinated derivatives (in the nucleus and chain are obtained). The conversion of the m-xylene is 90.6%. The yield of monochloroxylene is 69.2%, and of dichloroxylene is 17.1%.

EXAMPLE 2

(a) Chloroamine is prepared as described in example 1 starting from 0.428 moles of meta-xylene, 0.304 moles of monochloroxylene, 0.07 moles of nuclear monochlorinated derivative and 1.8 moles of diisobutylamine.

(b) 0.06 moles of ground $FeSO_4.7H_2O$ and 3.5 moles of 98% $H_2SO_4$ are fed into a 2 l flask. While maintaining the reaction mixture temperature between 0° and $+5°$ C., the mixture of xylene and its chlorinated derivatives and chloroamine is added under strong stirring. The addition terminates after 28 mins. After a further 30 mins. of agitation (always at the same temperature), the mixture is poured into water and ice, and extracted with ether. The ether phase is concentrated and analysed by the gas chromatograph using the internal standard method. The reaction product is found to be composed of 0.021 moles of m-xylene, 0.091 moles of derivative monochlorinated in the nucleus, 0.370 moles of monochloroxylene, 0.237 moles of dichloroxylene, and 0.063 moles of mixed dichlorinated derivatives.

With respect to the fresh m-xylene fed at the beginning of the test, the yield of monochloroxylene is 15.5%, and of dichloroxylene is 55.4%.

EXAMPLE 3

(a) Chloroamine is prepared as described in example 1 from 0.65 moles of m-xylene, 1.3 moles of dicyclohexylamine and sodium hypochlorite.

(b) The solution of chloroamine in m-xylene is fed gradually by means of a teflon metering pump into a 2 liter flanged reactor cooled to 0° C., fitted with a turbine stirrer, reflux condenser, immersed thermometer and nitrogen inlet, and containing 0.24 moles of FeSO$_4$.7H$_2$O and 4.8 moles of 98% H$_2$SO$_4$. The feed lasts for 50 mins. The mixture is stirred for a further 10 mins. (While continuously maintaining the reaction mixture temperature between 0° and +5° C.). The mixture is then poured into ice. It is extracted with ether, the ether solution is concentrated and is analysed by the gas chromatograph using the internal standard method. A m-xylene conversion of 96%, a monochloroxylene yield of 40% and a dichloroxylene yield of 40.2% in molar terms are found.

EXAMPLES 4–12

The reactions are carried out under the conditions already illustrated. Operating parameters and results are shown in the following table.

EXAMPLE 14

0.184 moles of FeSO$_4$.7H$_2$O and 7.07 moles of 98% sulphuric acid are fed into a flask equipped as in the preceding examples. A mixture of 2.11 moles of diisopropylchloroamine (prepared as described in the preceding examples), 1 mole of xylene and 2.73 moles of nitromethane is then gradually added while stirring and maintaining the temperature between −3° and +3° C. When the addition is complete, the mixture is stirred for a further two hours while maintaining the indicated temperature. The reaction mixture is then treated and analysed as described in the preceding examples. Yield of dichloroxylene 47.8%, of monochloroxylene 18.8%.

EXAMPLE 15

By operating as in example 14, but with a m-xylene/diisopropylchloroamine/98% H$_2$SO$_4$/FeSO$_4$.7-

TABLE

EXAMPLES 4–12

| | amine type | temp. | molar reagent ratios H$_2$SO$_4$/chloroamine/m-xylene/FeSO$_4$.7H$_2$O | yield mol % monochloroxylene | dichloroxylene |
|---|---|---|---|---|---|
| 4 | diisobutyl | 0/+5° C. | 7.2/1.2/0.6/0.24 (96%) | 16.3 | 51.0 |
| 5 | cyclohexylisopropyl | −1/+1° C. | 1.2/0.36/0.15/0.06 (98%) | 30.3 | 45.2 |
| 6 | dicyclohexyl | −1/+1° C. | 1.2/0.36/0.15/0.06 (98%) | 50.0 | 45.0 |
| 7 | dicyclohexyl | −1/+1 | 4.8/1.2/0.6/0.24 (98%) | 44.4 | 39.7 |
| 8 | diisobutyl | −4/+1 | (3.6 + 1.2)/1.2/0.6/0.24 (96% 100%) | 48.0 | 36.0 |
| 9 | diisobutyl | −1/+1 | 4.8/1.2/1.2/0.24 (88%) monochloroxylene | conversion 50% | 41.3 |
| 10 | diisobutyl | 0/+5° | 4.8/1.2/0.34/0.24 (98)% +0.52 monochloroxylene | 13.8 (calculated with respect to the xylene) | 111.8(*) |
| 11 | tetramethylpiperazine | −1/+1 | 1.2/0.36/0.15/0.06 | 67 | 26 |
| 12 | diisobutyl | −1/+1 | 1.2/0.36/0.15/0.06 (98%) | 26 | 52 |

(*)The yield is formally greater than 100% because the monochloroxylene also gives a good yield of dichloroxylene.

EXAMPLE 13

(a) 700 ml of water and 88.10 g of Ca(OCl)$_2$ are fed into a 1 l flask fitted with a stirrer, immersed thermometer, reflux condenser and dropping funnel, the temperature being maintained at 15°–20°. 30 g of m-xylene are added, followed gradually by 87.17 g of diisobutylamine while always checking the temperature. When the addition is complete, stirring is again continued for one hour, CO$_2$ then being bubbled through for 15–20 mins. while maintaining the temperature between 10° and 15°. The mixture is diluted to double its volume with water, the organic phase is separated and washed firstly with a 5% ammonium sulphate solution, then with distilled water.

(b) The chloroamine-xylene mixture (see point a) is added to a flask containing 33.6 g of FeSO$_4$ in 70 ml of 98% H$_2$SO$_4$, while maintaining the temperature between −1° and +1° C. and vigorously stirring. The addition lasts about 15 mins. Stirring is continued for a further 45 mins. while still maintaining the temperature around 0° C. The reaction mixture is then treated as in example 1, and the concentrated organic phase is analysed by a gas chromatograph using the internal standard method. The yield of monochloroxylene is 26.7% and of dichloroxylene is 51.0%.

H$_2$O/CH$_3$NO$_2$ ratio of 1/2.2/7.36/0.184/5.7 and reacting for 150 mins between −5° and 0° C., a dichloroxylene yield of 53.8% and a monochloroxylene yield of 11.1% (molar) are obtained.

EXAMPLE 16

6.72 g of FeSO$_4$.7H$_2$O (0.23998 moles) and 367.76 g of 96% H$_2$SO$_4$ (3.59998 moles) are fed under a stream of nitrogen into a 2 l cylindrical glass reactor fitted with a teflon turbine stirrer, thermometer, nitrogen inlet, condenser, a 100 cc glass dropping funnel and a 500 cc jacketed dropping funnel. The mixture is cooled to −2° C. with an alcohol and dry ice refrigerating bath maintained at −40° C., and 117.96 g of 100% H$_2$SO$_4$ (1.20288 moles) at 20° C. and 256.44 g of a solution of 63.85 g of para-xylene (0.60140 moles) and 192.56 g of N-chlorodiisobutylamine (1.17593 moles) at 0° C. are fed separately and simultaneously from the dropping funnels (final molar feed ratio of H$_2$SO$_4$/N-chlorodiisobutylamine/para-xylene/FeSO$_4$.7H$_2$O is 7.99/1.96/1/0.40). Feeding is carried out over 45 mins. under strong stirring (about 1900 rpm) while maintaining the temperature between 0° and +5° C. The reaction is allowed to proceed for a further 15 mins., and is stopped by pouring the reactor contents into a beaker containing about 1200 cc of wet ice. The mixture is extracted with ethyl ether (6-7 times with 100 cc portions) until the organic phase is completely recovered. The organic phase is dried with anhydrous $Na_2SO_4$, filtered from it and concentrated in a Vigreux column of ⌀ 26, 20 cm at 500 torr, with a maximum boiler temperature of 30° C.

The boiler residue is analysed by the gas chromatograph using the internal standard method in a glass column with 15% CBW 20M on CHROMOSORB W 60-80 mesh ⌀ 2 mm, 1=3 m. The analysis shows the following:

conversion of para-xylene = 99.5 mol %
chloropara-xylene/para-xylene yield = 16.1 mol %
α, α'-dichloropara-xylene/para-xylene yield = 34.0 mol %.

EXAMPLE 17

The following was obtained on operating as in example 1 but using ortho-xylene instead of para-xylene as the aromatic substrate:

| Feed: | | |
|---|---|---|
| Ground $FeSO_4.7H_2O$ | 66.72 g (0.23998 moles) | charge in reactor (fed at 20° C. over 32 mins. during the course of the test) |
| 96% $H_2SO_4$ | 367.76 g (3.59998 moles) | |
| 100% $H_2SO_4$ | 117.96 g (1.20288 moles) | |
| N—chlorodiisobutylamine | 197.17 g (1.20411 moles) | fed at 0° C. over 32 mins. |
| ortho-xylene | 64.01 g (0.60290 moles) | |
| Total | 261.18 g | |

Molar ratio $H_2SO_4$/N-chlorodiisobutylamine/ortho-xylene/$FeSO_4.7H_2O$ = 7.97/2.0/1/0.40.

Gas chromatograph analysis gave:

| ortho-xylene conversion | 99.5% |
|---|---|
| chloroortho-xylene yield | 42.1% |
| α,α'-dichloroortho-xylene yield | 22.9% |

We claim:

1. A process for the selective polyhalogenation of an alkylbenzene having at least two alkyl chains so as to place a single halogen atom on each alkyl chain which comprises reacting an alkylbenzene with an N-halogenamine at a temperature of from −20° C. to +40° C. in the presence of a proton donor and of a catalyst constituted of a metal ion which is capable of existing in various oxidation states but which is in a lower oxidation state, the quantity of said catalyst varying from 1 to 50 mol % with respect to the alkyl side chains of the starting alkylbenzene, the molar ratio of said proton donor to said N-halogenamine being between 1.2 and 8.

2. A process as claimed in claim 1 wherein the proton donor is acetic acid, trifluoroacetic acid, mixtures thereof, or sulfuric acid, wherein said N-halogenamine derives from a primary or secondary amine with sufficient steric bulk and chain which has no C—H bonds in the delta position to the nitrogen atom, wherein the catalyst is constituted of a metal ion chosen from $Fe^{2+}$, $Cu^+$, $Cr^{2+}$, $Ti^{3+}$ and $V^{2+}$, and wherein said alkylbenzene is selected from m-xylene, m-diisopropylbenzene, p-diisopropylbenzene, m-diethylbenzene, p-diethylbenzene, p-xylene, ethylbenzene and isopropylbenzene.

3. A process as defined in claim 2 wherein said alkylbenzene is m-xylene or p-xylene, the reaction is carried out at a temperature between −10° C. and +10° C., and a halogen atom is on each methyl group.

4. A process as defined in claim 2 wherein said proton donor is sulfuric acid at a concentration between 80 and 96%.

5. A process as defined in claim 2 wherein the molar ratio of said N-halogenamine is substantially the same as that of the alkyl side chains of the starting alkylbenzene.

6. A process as defined in claim 2 wherein said primary or secondary amine is diisopropylamine, diisobutylamine, diterbutylamine, dipropylamine, dicyclohexylamine, cyclohexylpropylamine, cyclohexylisopropylamine, cyclohexylmethylamine, cyclohexylethylamine, tetramethylpiperidine, piperidine, dibenzylamine, benzylethylamine or benzylpropylamine.

7. A process as defined in claim 2 wherein the reaction is carried out in the presence of an organic solvent chosen from esters, halogen or nitro derivatives of hydrocarbons, and nitriles.

* * * * *